United States Patent [19]
Foo et al.

[11] Patent Number: 6,136,989
[45] Date of Patent: Oct. 24, 2000

[54] METHOD FOR HIGH YIELD AND LARGE SCALE EXTRACTION OF PACLITAXEL FROM PACLITAXEL-CONTAINING MATERIAL

[75] Inventors: Samuel Siang Kiang Foo, Vancouver; Yili Bai, Richmond; Martin Ehlert, Cambridge, all of Canada

[73] Assignee: Phytogen Life Sciences, Incorporated, Delta, Canada

[21] Appl. No.: 09/223,694

[22] Filed: Dec. 30, 1998

[51] Int. Cl.$^7$ .................................................. C07D 305/14
[52] U.S. Cl. ............................................. 549/510; 549/511
[58] Field of Search ..................................... 549/510, 511

[56] References Cited

U.S. PATENT DOCUMENTS

| | | | |
|---|---|---|---|
| 5,279,949 | 1/1994 | Nair | 435/123 |
| 5,281,727 | 1/1994 | Carver et al. | 549/510 |
| 5,380,916 | 1/1995 | Rao | 560/107 |
| 5,393,895 | 2/1995 | Gaullier et al. | 549/510 |
| 5,393,896 | 2/1995 | Margraff | 549/510 |
| 5,440,055 | 8/1995 | Castor | 549/510 |
| 5,445,809 | 8/1995 | Strobel et al. | 424/1.81 |
| 5,451,392 | 9/1995 | Strobel et al. | 424/181 |
| 5,453,521 | 9/1995 | Gaullier et al. | 549/541 |
| 5,466,455 | 11/1995 | Huffstutler, Jr. et al. | 424/401 |
| 5,475,120 | 12/1995 | Rao | 549/510 |
| 5,478,736 | 12/1995 | Nair | 435/123 |
| 5,480,639 | 1/1996 | ElSohly et al. | 424/195.1 |
| 5,549,830 | 8/1996 | Carver et al. | 210/641 |
| 5,561,055 | 10/1996 | Page et al. | 435/252.1 |
| 5,580,899 | 12/1996 | Mayhew et al. | 514/499 |
| 5,618,538 | 4/1997 | ElSohly et al. | 424/195.1 |
| 5,620,875 | 4/1997 | Hoffman et al. | 435/123 |
| 5,642,587 | 7/1997 | Janes et al. | 47/58 |
| 5,654,448 | 8/1997 | Pandey et al. | 549/510 |
| 5,670,673 | 9/1997 | Rao | 549/510 |
| 5,723,635 | 3/1998 | Durand et al. | 549/510 |
| 5,736,366 | 4/1998 | Margraff | 435/123 |
| 5,744,333 | 4/1998 | Cociancich et al. | 435/123 |

FOREIGN PATENT DOCUMENTS

| | | |
|---|---|---|
| 1124735A | 6/1996 | China . |
| 11401701 | 1/1997 | China . |
| 521 675 A1 | 1/1993 | European Pat. Off. . |
| 553 780 B1 | 8/1993 | European Pat. Off. . |
| 700 910 A1 | 3/1996 | European Pat. Off. . |
| 717 041 A1 | 6/1996 | European Pat. Off. . |
| WO 92/07482 | 5/1992 | WIPO . |
| WO 94/13827 | 6/1994 | WIPO . |
| WO 94/20486 | 9/1994 | WIPO . |
| WO 95/26794 | 10/1995 | WIPO . |
| WO 95/31993 | 11/1995 | WIPO . |
| WO 96/34973 | 11/1996 | WIPO . |
| WO 97/09443 | 3/1997 | WIPO . |
| WO 98/07712 | 2/1998 | WIPO . |

OTHER PUBLICATIONS

Chen and Kingston, "Isolation And Structure Elucidation Of New Taxoids From *Taxus Brevifolia*," *Journal of Natural Products* 57(7):1017–1021, 1994.

Huang et al., "New Taxanes From *Taxus Brevifolia*, 2$^1$," *Journal of Natural Products* 49(4):665–669, 1986.

Kingston et al., "Modified Taxols, 7$^1$. A Method For The Separation Of Taxol And Cephalomannine," *Journal of Natural Products* 55(2):259–261, 1992.

Rao, "Taxol and Related Taxanes. I. Taxanes of *Taxus brevifolia* Bark," *Pharmaceutical Research* 10(4):521–524, 1993.

Rao et al., "A New Large–Scale Process for Taxol and Related Taxanes form *Taxus brevifolia*," *Pharmaceutical Research* 12(7):1003–1010, 1995.

*Primary Examiner*—Ba K. Trinh
*Attorney, Agent, or Firm*—Seed Intellectual Property Law Group PLLC

[57] ABSTRACT

A method of isolating paclitaxel from pactitaxel-containing material that includes the steps of obtaining an acetone mixture of the paclitaxel-containing material, then mixing the acetone mixture with an aqueous solvent to form an aqueous supernatant and a precipitate, wherein the precipitate contains at least 3-times higher paclitaxel content than the paclitaxel extract. The acetone/water precipitation step provides a high yield of highly pure paclitaxel that is suitable for industrial scale isolation using conventional normal-phase silica chromatography steps, and the preparation of pharmaceutical compositions containing paclitaxel.

61 Claims, No Drawings

METHOD FOR HIGH YIELD AND LARGE SCALE EXTRACTION OF PACLITAXEL FROM PACLITAXEL-CONTAINING MATERIAL

TECHNICAL FIELD

This invention relates to methods for industrial-scale isolation of paclitaxel from paclitaxel-containing material and the preparation of a highly pure paclitaxel composition suitable for pharmaceutical formulation.

BACKGROUND OF THE INVENTION

The complex diterpene pseudoalkaloid paclitaxel is the most important antineoplastic agent discovered in the last 20 years. It is present in the plant tissue of the family Taxaceae, especially in several species of Yew trees and shrubs that comprise the genus Taxus. While many of the taxanes possess cytotoxic properties making them useful for therapeutic treatment of cancers, paclitaxel has been the subject of the greatest study and was the first to obtain regulatory approval for clinical use.

Regulatory standards for pharmaceutical formulations of natural products isolated from plant sources are highly demanding in terms of reliability of production methods and purity of the sample obtained, especially where (as with paclitaxel) the source material contains other cytotoxic compounds of similar structure and biological activity. Extracts of Yew plants typically contain several taxanes including, for example, baccatin III, cephalomannine, 10-deacetyl taxol ("10-DAT"), 10-deacetyl baccatin III, 7-epi-10-deacetyl taxol ("7-epi-10-DAT"), 7-epi-paclitaxel and taxol-C. Such compounds are difficult to separate from paclitaxel on an economical scale. The desired paclitaxel composition for human use requires isolation methodologies that reproducibly yield paclitaxel preparations containing at least 98.5% with low levels of taxane impurities. Furthermore, regulatory standards demand very low levels of residual solvents, such as methanol, hexane and acetone, which are typically used in the extraction of paclitaxel.

In addition to meeting regulatory requirements for reproducibility and purity, economic considerations demand that paclitaxel isolation methodologies be as simple and inexpensive as possible. Taxol is present in very low amounts in Yew plants. Thus, even when using tissue having a relatively high paclitaxel content, such as the bark of T brevifolia, and T. yunnanensis trees (about 0.02%) or the needles and roots of T. x media Hicksii shrubs (0.005–0.15%), very large amounts of paclitaxel-containing material must be harvested to obtain relatively small amounts of paclitaxel. This economic cost is exacerbated by the fact that conventional protocols for extraction and purification of paclitaxel are inefficient in terms of yield and/or require expensive materials and equipment, making industrial scale preparation of pharmaceutical grade paclitaxel extremely expensive. Procedures that rely on less inexpensive materials, such as solvent extractions followed by normal phase silica columns, typically result in paclitaxel preparations of low purity, low yield or both. Alternative procedures for improving yield and purity often rely on methods that are impractical and/or expensive on an industrial scale.

A large scale operation requires a robust procedure that is simple, inexpensive, reproducible, and provides a high yield and high level of purity. High yield and high purity are often at odds. High yield in a multistep procedure ideally requires high recovery for each intermediate step. Unfortunately, high recovery obtained by solvent extractions and partitions of paclitaxel often yields bulk fractions containing large amounts of impurities, especially those with related structures. To obtain high purity from these bulk fractions requires using chromatographic procedures that can resolve closely related components. However, chromatography media such as silica, which is relatively inexpensive and can be disposed of after use (thus avoiding regeneration), does not have effective resolving power if the feed materials are not previously enriched for paclitaxel. This often requires use of intervening steps that improves purity but sacrifices yield.

Large scale isolation of paclitaxel from more than 8000 lbs of bark by use of solvent extractions, differential crystallization and normal phase silica chromatography was described by Huang et al., (Journal of Natural Products 49(4): 665–669, 1986). This method demonstrated the general solubility and chromatographic properties of paclitaxel, and illustrated the difficulty encountered in obtaining a good yield of highly purified material using conventional techniques. Most subsequent techniques are essentially modifications of the Huang et al. method that have shown increased yields and/or purity. However, these methods still fall short of providing a satisfactory process for large scale isolation. Furthermore, most of the improved methods are based on laboratory scale experimentation that poorly translates into an efficient large scale production.

For example, the laboratory scale procedures described in U.S. Pat. Nos. 5,279,949 and 5,478,736 to Nair (also PCT Publication No. WO 97/09443) use activated charcoal for decolorizing an initial 70% ethanol/water extract and early filtration through Celite. The decolorized extract is subsequently extracted with ethyl acetate, and evaporated to precipitate taxanes. The taxanes are redissolved in ethyl acetate and loaded onto a first silica column that is eluted with a hexane/ethyl acetate gradient, and further purified by tandem silica columns or, alternatively, by reverse phase chromatography. Unfortunately, the procedure of Nair is not amenable to industrial scale isolations for several reasons. First, the amount of charcoal required (up to about 5%–15% w/v extract) creates processing, cleanup and flow problems when used on an industrial scale. In addition, neither the charcoal nor subsequent steps aid in removing key impurities that are difficult to separate and remain as persistent impurities even after purification over tandem silica columns. As a result, the final product obtained using three normal phase silica chromatography steps is not sufficiently pure for pharmaceutical preparations. Therefore HPLC and/or reverse phase chromatography is further recommended, which inevitably results in a lower yield of material and significantly increases the cost. Overall, the laboratory scale process described by Nair is extremely impractical and expensive on large scale.

U.S. Pat. Nos. 5,618,538 and 5,480,639 to ElSohly et al. provide several laboratory-scale examples related to isolating paclitaxel and other taxanes that include evaluation of a variety of plant species, plant parts, solvent systems for initial extraction, mechanical methods for extraction, and solvents for paclitaxel partitioning. The crude solvent extracts obtained are further subjected to Celite absorption followed by three normal phase silica chromatography steps using hexane/acetone, methanol/methylenechloride, and ethylacetate/methylenechloride as carrier solvents. The eluates from column fractions are evaporated before proceeding to the next step, and are not subject to intervening precipitation or crystallization steps to enhance purity. A final yield of 26 mg of paclitaxel described as "pure" by HPLC analysis was obtained from 500 g of T media "dark green spreader"

leaves having a starting paclitaxel content of 0.0074%. Thus, this procedure represents a method for recovery of about 70% of the paclitaxel present in the initial plant material. However, although the procedure provides a high yield of paclitaxel, it requires up to four repeated chromatographic steps. In addition, the use of large amounts of celite, silica and solvents relative to other methods is a significant hindrance for implementing this process on large scale.

The procedures described in U.S. Pat. Nos. 5,380,916, 5,475,120, and 5,670,673 to Rao (also PCT Publication No. WO 92/07842) use a series of solvent extractions employing ethanol, chloroform, ligroin, benzene and methanol followed by reverse phase chromatography exemplified using HPLC with an acetonitrile eluent. However, reverse-phase chromatography is not practical for large scale preparation of paclitaxel primarily because plant extracts from Yew contain numerous substances that interfere with column performance and maintenance. Furthermore, reverse-phase chromatography media is expensive and not easily regenerated, thus creating high replacement costs, and large scale production based on an acetonitrile eluent is not practical unless total containment is provided, which is very costly. Rao reports a yield of about 0.05% of the biomass as paclitaxel, but still further refinement is needed to obtain pharmaceutical grade paclitaxel. As a general principle, only those processes shown to produce high purity paclitaxel on a very large scale are suitable candidates for industrial production, because large scale generally has an adverse effect on product quality compared to the same process executed on small scale.

The procedure described in PCT Publication No. WO 96/34973 by hong et al. involves use of a preliminary treatment of a methanol/dichloromethane extracts with a synthetic absorbent, such as activated charcoal or clay, followed by multiple dichloromethane washings and precipitations, first using hexane to produce a 23% paclitaxel precipitate, then using multiple alcohol/water fractional precipitations to produce an 85% extract suitable for final purification of paclitaxel by HPLC. This procedure is also unsuitable for large scale preparation, not only because of the use of activated charcoal having the drawbacks indicated above, but because hexane and alcohol/water precipitation steps have been found to give irreproducible results. In addition, the procedure is inefficient and costly because of the time and materials required for multiple precipitation steps (each requiring several days and large quantities of solvent), and the expense of HPLC techniques applied on an industrial scale.

It should be noted that Hong et al., in the abstract, refer to "a high recovery of over 90%", but a closer examination reveals that this recovery rate is characteristic for only the best step yields and that the overall yield is much lower. Hong et al. report cases of step yields at 100%. Such quantitative yields can sometimes be obtained in the laboratory by the use of relative large quantities of auxiliary materials, the application of very costly and effective techniques (such as HPLC), or the use of time consuming and/or labor intensive methods. All these aspects are apparent in the process described by Hong et al., thus emphasizing that, while the procedure may be suitable for laboratory practice, it is of very limited utility for large scale production.

The procedure described in PCT Publication No. WO 98/07712 by Zamir uses an organic extraction followed by an aqueous wash, charcoal treatment, and precipitation/recrystallization of taxanes in the presence of non-polar solvents such as toluene and ether. Finally, a recrystallized fraction is subjected to either reverse phase chromatography or HPLC (or both) to separate a variety of taxanes including paclitaxel. This procedure has many of the drawbacks mentioned above, including the use of charcoal (which requires an additional cleaning step to remove fine charcoal particles), and the use of expensive reverse phase and HPLC systems to obtain paclitaxel of sufficient purity. In addition, the extensive use of methylene chloride and acetonitrile throughout the process requires expensive containment.

The procedure described in Chinese Application No. 96102442.9 by Liu and Yang relies on the use of porous polymer reverse-phase chromatography early in an extraction process. An alcohol extract is partitioned into dichloromethane, subjected to an aqueous wash, filtered and immediately loaded onto a porous polystyrene reverse-phase column which is eluted with increasing steps of methanol/water. A paclitaxel fraction eluted from the column containing 50–68% paclitaxel contained about 10% cephalomannine, and a fraction containing 60% cephalomannine contained about 10% paclitaxel. Another fraction containing 30% 10-deacetyl baccatin III may be precipitated in acetone and water to obtain 76% 10-deacetyl baccatin-III. Further purification of paclitaxel required an additional reverse phase step to yield a fraction containing about 98% paclitaxel. However, this is not sufficiently pure for pharmaceutical purposes, especially when the remaining 2% impurities likely contain cephalomannine.

The procedures described in U.S. Pat. Nos. 5,393,896 and 5,736,366 to Margraff and U.S. Pat. Nos. 5,453,521 and 5,393,895 to Gaullier et al. are related to the isolation of 10-deacetyl baccatin III which is useful as a precursor for chemical synthesis of paclitaxel. The processes described therein are specifically directed to isolation of the precursor molecule using alcohol extraction of paclitaxel-containing material, an aqueous wash, organic solvent extraction, and selective precipitation. The methods are not instructive for the isolation of paclitaxel, but do illustrate the difficulty encountered in separating taxane compounds obtained from extracts of Yew.

The procedure described by Shibuya in European Pat. Publication No. 700 910-A1 relates to extracting paclitaxel from *T. sumatrana*, using solvent extraction, liquid-liquid partitioning, silica chromatography, Sephadex chromatography and reverse phase HPLC to obtain a paclitaxel yield of only 0.006%. The low yield again illustrates the difficulty in creating methodologies for the efficient extraction of paclitaxel from plant material using reverse phase and HPLC techniques. Again, this method is very impractical and expensive for large scale production.

The procedure of U.S. Pat. No. 5,744,333 and European Patent No. 553,780 B1 to Cociancich and Pace provides a method of isolating paclitaxel and related compounds from tissues of ornamental Taxus plants, such as *T. x media Hicksii* or *T. cuspidata* and cultures prepared therefrom. The steps include making a methanol extract of the plant material, vacuum drying the methanol extract, performing a liquid-liquid extraction with cyclohexane and methylenechloride, followed by silica gel HPLC chromatography to obtain purified paclitaxel, though not of pharmaceutical grade. Similarly Chinese Application No. 94114041.5 by Lu et al. describes a general method for obtaining a 0.007% yield of paclitaxel having greater than 98% purity from *T. floridana* or *T. mairei*, using solvent extraction followed by reverse phase silica chromatography or reverse phase HPLC. Again, the drawbacks of HPLC and reverse phase chromatography as employed in these references have been mentioned above.

Accordingly, there is a need in the art for paclitaxel purification methods that can be used on a very large scale, that are rapid, that employ conventional low to medium pressure normal-phase chromatography, that use inexpensive materials, and that provide reproducible isolation of a paclitaxel composition having pharmaceutical grade purity and a high yield. The present invention fulfills these needs and provides further related advantages.

SUMMARY OF THE INVENTION

The present invention is generally directed to methods for high yield and large scale extraction of paclitaxel from paclitaxel-containing material including, but not limited to, paclitaxel-containing plant tissue, cells from plant cell culture and microorganisms that produce paclitaxel. More specifically, this invention provides the unexpected discovery that an acetone/water precipitation of an acetone mixture containing at least 5% (w/w) paclitaxel will provide a precipitate containing at least 20% (w/w) paclitaxel, and that an acetone/water precipitation of an acetone mixture containing at least 10% (w/w) paclitaxel will provide a precipitate containing at least 40% (w/w) paclitaxel and, more typically, at least 50% (w/w) paclitaxel. This results in a high yield and high purification at an early step of paclitaxel purification, and provides for economical large scale isolation of pharmaceutical grade paclitaxel from paclitaxel-containing materials using conventional chromatographic methods.

In one aspect, the invention provides a method for isolating paclitaxel from a paclitaxel extract that includes the steps of: adding acetone to the paclitaxel extract to form an acetone mixture; contacting the acetone mixture with an aqueous solvent to form a supernatant and a precipitate, wherein the precipitate has a paclitaxel purity that is at least 3 times higher than the paclitaxel purity in the paclitaxel extract, and recovering the precipitate. In one embodiment, the paclitaxel extract contains at least 5% (w/w) paclitaxel and the precipitate contains at least 20% (w/w) paclitaxel. In another embodiment, the paclitaxel extract contains at least 10% (w/w) paclitaxel and the precipitate contains at least 40% (w/w) paclitaxel. In still another embodiment, the precipitate has a paclitaxel purity that is as at least 4 times higher than the paclitaxel purity in the paclitaxel extract.

In a related aspect, the paclitaxel extract is obtained from a paclitaxel-containing material. Paclitaxel-containing material suitable for the practice of the method includes any tissue from a species of a Taxus genus, as well as tissue cultured from such a species and microorganisms that produce paclitaxel. Typically the paclitaxel-containing material includes tissue from the species *T. brevifolia, T. yunnanensis, T. x media Hicksii, T. x media* "dark green spreader," *T. x media* Hill, *T. chinensis, T. wallichiana T. canadensis* and *T. cuspidata.* When the species is *T. brevifolia,* or *T. yunnanensis* the tissue is typically bark. When the species *T. x media Hicksii, T. x media* Hill, *T. x media* dark green spreader or *T. cuspidata* the tissue is typically roots and/or needles, though any tissue with extractable paclitaxel can be used. In other embodiments, the paclitaxel-containing material may be obtained from a cell culture of a taxus species which may include the cells or a media in which the cell culture is grown. One embodiment of a cell culture is a root culture. In a related embodiment where the paclitaxel-containing material is a microorganism, the microorganism is a species of *Erwinia Taxi* or *Taxomyces andreanae.*

In one embodiment, the paclitaxel extract used to prepare the acetone mixture of this invention is obtained by eluting paclitaxel from at least one chromatography matrix, typically a silica matrix. In another embodiment, the paclitaxel extract is obtained by performing at least two crystallizations of paclitaxel from a mixture containing an organic solvent. Still other embodiments include eluting paclitaxel from at least one chromatography matrix and performing at least one crystallization of paclitaxel from a mixture containing an organic solvent. Typically, any of the embodiments for obtaining the paclitaxel extract may further include a step of performing at least one liquid-liquid extraction with an organic solvent to form a two phase solution wherein one phase is enriched with paclitaxel.

The aqueous solvent used to perform the acetone/water precipitation of this invention includes any solvent containing at least 50% (v/v) water. In most embodiments, the aqueous solvent contains at least 50% (v/v) water and, more typically, at least 70% (v/v) or at least 90% (v/v) water. In a more specific embodiment, the aqueous solvent consists essentially of water. Optionally, the aqueous solvent may be buffered. In certain embodiments, the acetone/water precipitation step includes adding about one to five volumes of aqueous solvent to one volume of acetone mixture. In more typical embodiments, two to three volumes of aqueous solvent is mixed with one volume of acetone. In a more specific embodiment, about two and one half volumes of aqueous solvent is mixed with one volume of acetone mixture.

In another aspect, the precipitate from the acetone mixture contains an amount of impurities that is less than the amount of impurities contained in the acetone mixture. Generally, the amount of impurities contained in the precipitate is less than about 50% of the amount of impurities contained in the acetone mixture. In one embodiment, the amount of impurities contained in the precipitate is about 75% less than the amount of impurities contained in the acetone mixture.

In yet another aspect, the precipitate provided by the above methods of this invention generally contains at least 90% of the paclitaxel present in the acetone mixture and more typically contains at least 95% of the paclitaxel present in the acetone mixture.

In a related aspect, this invention provides a method of making an acetone mixture containing at least 5% (w/w) paclitaxel that includes the steps of extracting a paclitaxel-containing material containing at least 0.005% (w/w) paclitaxel with methanol to obtain a methanol extract; partitioning the methanol extract by liquid-liquid extraction of the methanol extract with methylene chloride and water to form a two phase system having a methanolic phase containing methanol/water and a methylene chloride phase comprised of methylene chloride and paclitaxel; removing methanol and water from the methylene chloride phase to obtain a concentrated extract comprised of at least 1% paclitaxel, not more than about 5% (v/v) methanol, and not more than about 1% (v/v) water; contacting the concentrated extract with a silica matrix then eluting the silica matrix to obtain an eluate containing at least 5% (w/w) paclitaxel and adding acetone to the eluate to obtain the acetone mixture. In preferred embodiments, the eluate is dried to residue and acetone is added to dissolve the paclitaxel in the residue. Typical paclitaxel-containing material for the method of making the acetone mixture containing at least 5% (w/w) paclitaxel includes tissue selected from the Taxus species, cell cultures and microorganisms mentioned above.

In certain embodiments, the acetone mixture contains at least 10% (w/w) paclitaxel and typically contains at least 12.5% (w/w) paclitaxel. In another embodiment, the acetone mixture contains at least 90% of the paclitaxel present in the concentrated extract. In still another embodiment, the concentrated extract is prepared to have a methanol content ranging from 2.5 to 5% (v/v) and a water content ranging from 0.1 to 1% (v/v).

In yet another aspect, the invention provides an overall method for isolating paclitaxel from paclitaxel-containing material suitable for use on an industrial scale. The method includes the steps of: a) extracting paclitaxel-containing material with methanol to obtain a methanol extract; b) partitioning the methanol extract by liquid-liquid extraction of the methanol extract with methylene chloride and water to form a two phase system having a methanolic phase comprised of methanol/water and a methylene chloride phase containing paclitaxel; c) removing the water/methanol phase from the methylene chloride phase to obtain a concentrated extract comprised of at least 1% (w/w) paclitaxel, not more than about 5% (v/v) methanol, and not more than about 0.5% (v/v) water; d) contacting the concentrated extract with a first silica matrix and eluting the first silica matrix to obtain a first eluate containing at least 10% (w/w) paclitaxel; e) adding acetone to the first eluate to obtain the acetone mixture; f) contacting the acetone mixture with an aqueous solvent to form a precipitate containing at least 40% (w/w) paclitaxel; g) purifying paclitaxel from the precipitate by chromatography on a second silica column and eluting paclitaxel from the second silica column to form a second eluate containing at least 65% (w/w) paclitaxel; h) crystallizing the paclitaxel from the second eluate with pentane to form a first crystalline solid containing at least 85% (w/w) paclitaxel; i) purifying paclitaxel from the first crystalline solid by chromatography on a third silica column and eluting paclitaxel from the third silica column to obtain a third eluate containing at least 90% (w/w) paclitaxel; and j) crystallizing paclitaxel from the concentrate dissolved in acetone by mixing the third eluate with pentane to form a second crystalline solid containing at least 98.5% (w/w) paclitaxel.

In a preferred practice, the paclitaxel-containing material contains at least 0.005% (w/w) and more preferably at least 0.02% (w/w) paclitaxel. In certain practices, the first eluate is concentrated to a residue, and acetone is added to the concentrated residue. In most practices, at least one of the first eluate, the second eluate and the third eluate is concentrated to a residue before proceeding to the next step. Typically, at least one residue is dissolved in acetone.

In certain embodiments of the overall method, the second crystalline solid (final product) contains at least 40% of the paclitaxel present in the starting paclitaxel-containing material. In a typical embodiment, the second crystalline solid contains at least 60% of the paclitaxel present in the starting paclitaxel-containing material. In another aspect, the overall method of this invention provides that the second crystalline solid is comprised of at least 98.5% (w/w) paclitaxel. In more typical embodiments, the second crystalline solid is comprised of greater than 99.0% (w/w) paclitaxel and more preferably greater than 99.5% (w/w) paclitaxel. In another aspect, the second crystalline solid contains less than 0.2% of any individual taxane impurities. In certain embodiments the second crystalline solid contains less than 0.1% of any individual taxane impurities, and in still other embodiments, contains less than 0.05% of any individual taxane impurities. In yet another aspect, the overall method provides that an amount of paclitaxel recovered in each step of the method is typically at least 90% of an amount of paclitaxel present in an immediately preceding step.

In still another aspect, the present invention provides a paclitaxel composition that contains of at least 99.5% paclitaxel and total taxane impurities from 0.05 to 0.14%. Typically, total taxane impurities are from 0.06 to 0.09%. In certain embodiments, the paclitaxel composition contains at least 99.5% and from 0.01 to 0.05% cephalomannine, and more preferably from 0.01 to 0.03% cephalomannine. In related embodiments, the paclitaxel composition contains the aforementioned concentrations of paclitaxel and cephalomannine, and further contains no detectable amounts (i.e., less than 0.01%) of 10-DAT, 7-epi-10-DAT, or 7-epi-paclitaxel. In another embodiment the aforementioned compositions are prepared according to a method provided by this invention. The invention further provides these compositions formulated with a pharmaceutically acceptable carrier or diluent to yield a pharmaceutical composition containing paclitaxel suitable for administration to a warm-blooded animal, particularly humans.

These and other aspects of the present invention will be evident upon reference to the following detailed description. To that end, certain references are cited herein for purpose of clarity and completeness, and are each incorporated herein by reference in their entirety.

DETAILED DESCRIPTION OF THE INVENTION

Unless specified otherwise, the terms used herein have the meanings normally understood by those of skill in the art, including the meanings hereby defined:

"Paclitaxel Extract" refers to a composition obtained from a paclitaxel-containing material by treating the paclitaxel-containing material with at least one solvent.

A "residue" is material obtained by concentrating a starting material which is typically an extract, a fraction or an eluate which contains a desired material dissolved in a solvent. Typically, a residue may be formed by concentrating the starting material to dryness, however, any level of concentration constitutes formation of a residue.

"Purity" is a measure of the relative proportion of a particular species in a composition comprised of one or more species. Unless otherwise specified, purity is measured as the fractional weight of the particular species divided by the total weight of all solids expressed as a percentage (i.e., %).

"Percent" or "%", unless otherwise specified, refers to the weight/weight (w/w) purity for paclitaxel, or to the chromatographic area (measured at 227 nm) of a taxane impurity relative to the chromatographic area of the paclitaxel peak in an extract or final product. "Percent" or "%" does not include consideration of the weight of solvents added or removed from the extract. Thus, for example, an extract containing 10% paclitaxel may be diluted with a large volume of solvent, concentrated in a small volume of solvent or dried to a powder and in each case still be referred to as an extract containing 10% paclitaxel.

"Taxane impurity" refers to any one species of a non-paclitaxel taxane present in paclitaxel-containing material or an extract thereof, while the term "taxane impurities" refers to any two (or more) of the same. Typical taxane impurities include baccatin III, cephalomannine, 10-deacetyl taxol ("10-DAT"), 10-deacetyl baccatin III, 7-epi-10-deacetyl taxol (7-epi-1-DAT"), 7-epi-paclitaxel or taxol-C, as well as related metabolites, analogs and derivatives thereof.

"Total taxane impurities" refers to the total amount of a taxane impurity or taxane impurities.

"Precipitate" refers generally to material obtained in a solid phase by causing dissolved solutes to aggregate into a solid phase mass and fall out of solution. It also refers to the act of causing solutes to aggregate to form a precipitate. A precipitate is obtained from a starting material that is less than 98.5% pure and, more typically, less than 50% pure.

"Crystallize" and "crystallization" are used as ordinarily understood to mean formation of a solid phase mass from a solution wherein the solid phase mass is comprised of at least one chemical species in an ordered spatial array with respect to itself or another chemical species. The term may also be used in lieu of the term precipitation, especially where the solid phase mass obtained from solution has a purity of greater than 50%. Although the present description endeavors to maintain the distinction in the term precipitate and crystallize as they are commonly used in the art, it is understood that the description of the invention provided herein is not intended to be limited by these definitions. It is further understood that a precipitate may be comprised of crystallized material, that crystallized material may be comprised of non-crystallized precipitates, and that precipitation and crystallization may be used interchangeably to refer to the act of obtaining a solid phase material from a solution.

"Silica matrix" is a solid media containing a silicate which is used as an adsorbent or column material in chromatographic separations, including (but not limited to) ordinary silica, Florisil, porous silica gels or any physical formulation of a silicate for use in chromatographic procedures.

"Eluate" is material that is removed from an adsorbent or silica matrix by contacting the adsorbent with a mobile phase eluting solvent.

"Aqueous solvent" is a solvent comprised of at least 50% volume/volume (v/v) water and which may optionally contain solutes, other solvents, or both.

"Feed material" refers to material as it exists prior to being treated to a particular purification step.

"Paclitaxel-containing material" refers to selected parts of a plant, plant tissues, cell cultures, microorganisms or extracts with extractable paclitaxel.

"Pharmaceutical grade paclitaxel" is a paclitaxel composition meeting purity standards of a regulatory agency. An example purity standard is a composition comprised of at least 98.5% paclitaxel, less than 1% water, and no individual taxane impurity greater than 0.2%.

As mentioned above, this invention provides a method for a large scale isolation of pharmaceutical grade paclitaxel from paclitaxel-containing material using conventional normal-phase silica chromatography to produce a high yield of the paclitaxel present in the starting paclitaxel-containing material. A critical feature of the present invention is the use of an acetone/water precipitation step to obtain high yield and high purity of paclitaxel. The advantages of this invention include the use of normal-phase liquid chromatography and the ability to obtain pharmaceutical grade paclitaxel at a yield of at least 40% of the paclitaxel present in the starting paclitaxel-containing material. More typically, at least 60% of the paclitaxel present in the starting paclitaxel-containing material is obtained. These advantages translate into an economical process for industrial scale production of paclitaxel as exemplified by the large scale paclitaxel isolation methods described hereafter.

In some embodiments, the acetone/water precipitation step is used early in a paclitaxel isolation process so as to limit the number of subsequent steps required to obtain pharmaceutical grade paclitaxel. In other embodiments, the acetone/water precipitation step may be used later in an isolation process to aid in removal of residual impurities. In a typical embodiment, the acetone/water precipitation is used midway through an isolation procedure when some impurities have been removed and others remain. When used midway through an isolation process, the acetone/water precipitation step provides a high step purification of about four to five fold, a high step yield of at least 90% and more often at least 95%, and further provides substantial removal of unwanted impurities.

Because paclitaxel isolation is a multistep process and the acetone/water precipitation step is most effective midway through the process when an extract containing at least 10% paclitaxel has been obtained, it is convenient to describe the present invention as it is practiced in one embodiment that starts with the extraction of a starting paclitaxel-containing material. However, it should be understood that the invention is not limited in this manner, but rather disclosed in this manner merely for purpose of illustration.

1) Starting Paclitaxel-containing Material

Suitable paclitaxel-containing material for paclitaxel isolation according to the present invention is any tissue that contains a high paclitaxel content, preferably at least 0.005% of dried material. Examples of suitable paclitaxel-containing material include tissues from various species of Yew plants comprising the genus Taxus, most preferably the bark of *T. brevifolia*, or *T. yunnanensis*, and the roots and needles of ornamental Yew plants such as *T. cuspidata, T. x media* spp *Hicksii, T. x* dark green spreader and Hill., *T. chinensis, T. wallichiana, T. canadensis, T. globosa, T. sumatrana*, and *T. floridana*. Other suitable material include cultures of plant tissues obtained from a Taxus species. Methods for obtaining cultured tissue may be found for example in U.S. Pat. No. 5,744,333, European Patent No. 553,780 B1 to Cociancich and Pace and U.S. Pat. No. 5,451,392 to Strobel et al. The Strobel patent further provides for extracting paclitaxel from media in which cultured cells are grown which is also suitable for the practice of this invention. Also microorganisms expressing extractable paclitaxel are suitable, e.g., as cell paste or fermentation broth. One example of suitable microorganisms are species of Erwinia associated with some Taxus species as described in U.S. Pat. No. 5,451,392 to Page et al. Another example includes microorganisms of the genus Taxomyces, and more specifically, *Taxomyces andreanae*, which are capable of producing paclitaxel. Still other examples include microorganism engineered to produce paclitaxel using recombinant DNA techniques.

Although paclitaxel-containing material having at least 0.005% paclitaxel content is preferred, the acetone/water precipitation step of the present invention, may be used with any starting paclitaxel-containing material provided that an extract containing at least 5% paclitaxel can be prepared therefrom. (In this regard, and as mentioned above, the present invention incorporates each of the references provided in the Background section which describe tissues, species of Taxus, and/or methods of preparing extracts that are suitable for the practice of this invention.)

In a typical practice, the paclitaxel-containing material is either pulverized, chipped or otherwise ground into small pieces so as to increase efficiency of a solvent extraction. The paclitaxel-containing material may also optionally be dried. Paclitaxel-containing cell culture, cells, microorganisms and fermentation broths will typically be concentrated prior to solvent extraction. Cells and microorganisms can be processed as whole cells or cell paste or pulver.

2) Extraction

Paclitaxel-containing material is initially extracted by contacting the material with an organic solvent, usually for a prolonged period of at least 8 hours and typically for about 3 days with or without physical agitation to promote formation of a crude organic extract containing paclitaxel. The extraction may employ any of the solvent systems that have been previously described for the extraction of paclitaxel including but not limited to, acetone, methanol, ethanol, ethyl acetate, methylene chloride, chloroform, mixtures thereof, and mixtures containing an aqueous component of up to 60%. These solvents are typically added in an amount of about 4–20 liter per kg of the paclitaxel-containing material to prepare the crude organic extract. Reference is made for example, to the publications by Nair, ElSohly, Zamir, Rao, Slot, long, Lu, Liu and Yang cited in the Background which provide a non-exclusive description of several solvent systems that may be used to prepare an organic extract containing paclitaxel.

In one practice of this invention, the organic solvent is a polar organic solvent, typically an alcohol. For some embodiments, methanol is preferred because of its low cost, ease of removal and efficiency of paclitaxel extraction. In one embodiment, about 6–15 liters of methanol is added for every kg of paclitaxel-containing material to be extracted. The extraction is accelerated by agitating the paclitaxel-containing material, for example, by stirring or percolating the methanol with the paclitaxel-containing material for about 1–5 days at a temperature between room temperature and about 60° C., most typically at about 40° C. When the paclitaxel-containing material contains a paclitaxel content of at least 0.005%, methanol extraction for three days as described above recovers at least 90% of the available paclitaxel from the paclitaxel-containing material to form a crude methanol extract containing about 0.1–0.5% paclitaxel and having an overall solid content of about 0.5–5% (w/v).

The large volume of methanol extract thus obtained is optionally concentrated, typically about 10–30 fold by evaporation to obtain a methanol extract concentrate having a solid content of about 100–400 g/L.

3) Liquid-liquid Extraction

The crude organic extract is subsequently enriched for paclitaxel by performing 1–3 liquid-liquid extractions by mixing the organic extract with a non-miscible, organic solvent to form a two phase system wherein one phase contains paclitaxel. Generally, the two phase system includes a polar phase. Optionally, the paclitaxel-containing phase is selected and concentrated by evaporation to form a concentrated extract having a solid content of about 100–400 g/L and a paclitaxel purity of about 1–4%. In some embodiments, water is included to help remove preferentially water soluble materials and the less polar solvent is selected to remove undesirable compounds such as waxes, lipids, pigments, and sterols that are found in different amounts depending on the paclitaxel-containing material used. Typical solvents for liquid-liquid partitioning include hexane, hexanes, and methylene chloride. Methylene chloride has generally been found to be suitable for liquid-liquid extraction of paclitaxel-containing material especially when the solvent used for the crude organic extract is an alcohol.

The liquid-liquid extraction process causes a preferential enrichment of paclitaxel and results in about a 10 fold increase in paclitaxel purity of the concentrated extract to approximately 1–4% with a product yield of at least 90%. The concentrated extract obtained is optionally evaporated and the residue is redissolved in a solvent for loading onto a first silica chromatography matrix.

Other example methods of performing a liquid-liquid extraction are illustrated in U.S. Pat. Nos. 5,475,120, 5,380,916, and 5,670,673 to Rao and references cited therein, also in U.S. Pat. Nos. 5,618,538 and 5,480,639 to ElSohly and references cited therein. These methods or variants thereof may alternatively be used in lieu of the embodiments described in this invention. The only requirement for continuing with certain aspects of this invention is that the final concentrated extract have a paclitaxel purity of at least about 1%. In this regard, liquid-liquid extraction may be omitted altogether when a plant extract containing a paclitaxel purity of about 1% or higher is obtained by other methods such as for example, by intervening precipitation, crystallization or chromatography steps. One example of such a method is found in PCT Publication Nos. WO 98/07712 by Zamir which uses a precipitation step immediately after obtaining an initial organic extract to obtain a paclitaxel fraction that may be about 1% or higher.

First Silica Gel Chromatography to Obtain a 10% Acetone Mixture

The concentrated extract containing 1–4% paclitaxel is further purified by normal phase silica chromatography. As used herein, silica chromatography generally refers to the process of contacting a sample dissolved in a feed solvent with a silica matrix then eluting the silica matrix with an eluting solvent to obtain a fraction enriched with a desired component.

The dimensions of the first silica column are selected according to the quantity and purity of the solids to be separated. In one embodiment of a pilot scale process of the present invention, about 250 grams of solids are dissolved in about 0.75 liters of feed solvent which is then chromatographed over a Silica column of about 1.5- inches×10-feet. In another embodiment, about 40–50 kg of solids are dissolved in about 100–200 liters of feed solvent, and chromatographed over a Silica column of about 18-inches×10-feet.

It has also been shown that a layer of about 1–15 cm of Celite, preferably about 2–8 cm, on top of the silica column is recommended as a column prefilter which substantially decreases the loading time of the sample. It has further been shown that the optimal eluting solvent for the Silica column should be a hexane/acetone mixture at a ratio of about 3:1 and that "heart cut" fractions used for subsequent steps are those that lie between a first fraction containing at least 2% paclitaxel and a last fraction containing at least 2% paclitaxel. Pooling these fractions will typically yield a first column eluate comprising at least 5% paclitaxel, generally at least 10% paclitaxel, and more usually, at least 12.5% paclitaxel. Further data on these observations may be found in Examples 3 and 4.

One unexpected discovery of the present invention is that paclitaxel purification using normal phase silica chromatography with a hexane/acetone solvent system is affected by the concentration of methanol and water present in the concentrated paclitaxel extract used as feed material for the first silica column. Generally, there is an adverse effect on both recovery and purity if methanol is present at more than about 10% or if water is present at more than about 2%. This finding is important to large scale chromatography applications wherein the starting "feed" material is comprised of a relatively crude mixture. Upon concentration, such crude mixtures tend to gel, thus interfering with column flow. The addition of small amounts of methanol and water enhance the flow properties of the feed material. However, too much methanol or water interferes with column performance. Hence, optimizing methanol and water content is a further aspect of this invention.

Explorative data addressing different combinations of methanol and water are shown in Example 3. In one embodiment of this invention the presence of methanol in the feed material for a first silica chromatography column is reduced to 5% or below, in another embodiment, methanol is reduced to a range of about 2.5 to 5% and the water concentration is reduced to a range of about 0.1 to 1%. This generally provides a recovery of between 90% and 95% of the paclitaxel loaded onto the column and typically yields a column eluate having a paclitaxel purity of between 10% and 16.8%. More typically the recovery is at least 95% and the purity is at least 12.5%. To obtain the acetone mixture, the pooled fractions containing paclitaxel are concentrated by evaporation and dissolved in acetone.

One of ordinary skill in the art will recognize alternative methods for obtaining an acetone mixture containing at least 5% paclitaxel including the use of other purification methods. For example, the references provided in the Background of this invention all contain methods that will allow preparation of a fraction containing at least 5% paclitaxel that can be dissolved in acetone. Generally, these other methods include purification steps subsequent to obtaining a crude organic extract. In some embodiments, these steps include other chromatography steps such as a reverse-phase. HPLC, or ion exchange columns. Most typically, the column will contain a silica matrix though other matrix types can be used. in other methods, column chromatography is not needed to obtain a 5% extract. Typically these methods include performing at least two precipitations or crystallizations from an organic extract. In other methods, both a chromatography step and at least one precipitation step are required to obtain a 5% extract. In a typical procedure, any of the above methods are combined with a liquid-liquid extraction so as to yield an extract containing at least 10% paclitaxel. Any such extract may be dissolved in acetone to form an acetone mixture for use in a further embodiment of this invention.

5) Acetone/Water Precipitation

As noted above, a critical aspect of the present invention is the discovery that precipitation of an acetone mixture containing at least 5% paclitaxel with an aqueous solvent can provide a precipitate containing at least 20% and that precipitation of an acetone mixture containing at least 10% paclitaxel with a aqueous solvent can provide a precipitate containing at least 40% and more typically at least 50% paclitaxel. Furthermore, the precipitation can be performed with a high efficiency to obtain at least a 90% yield. In one embodiment, this discovery is used as a step to produce at least a 3-fold purification in paclitaxel. More often at least a 4-fold purification is obtained. The aqueous solvent should contain 50%–100% water. Typically the aqueous solvent contains at least 70% (v/v) water and preferably the aqueous solvent contains at least 90% (v/v) water. In one embodiment, the aqueous solvent is water. Optionally, the aqueous solvent can be buffered. Generally, about 1–5 volumes of aqueous solvent are added to one volume of acetone mixture. More specifically, the volume of aqueous solvent to use will depend on the constituent content of the acetone mixture and the presence of other solvents in the mixture. Typically, about 2–3 volumes of aqueous solvent are added to the acetone mixture. In one preferred practice, about 2.5 volumes of aqueous extract is added per volume of acetone mixture. In further embodiments, the aqueous solvent may be buffered.

In one embodiment of this invention, the acetone/water precipitation step is performed with high recovery rates when water is mixed with an acetone mixture to obtain an acetone to water ratio of about 2–3. In one embodiment, the acetone to water ratio is 1 to 2.5 which produces a slightly higher recovery rate in the results illustrated here. Table 1 illustrates that in experiments using the same acetone mixture obtained from a first silica column, a recovery of at least about 90% is obtained with an acetone to water ratio of 1 to 2 and recoveries of about at least 95% or greater are obtained using an acetone to water ratio of 1 to 2.5 or greater. The high recovery rates for the different ratios of acetone/water illustrated in Table 1 indicate that the amount of water used in an acetone/water precipitation can be further optimized for other paclitaxel isolation protocols.

TABLE 1

|  | Starting Material | | Acetone | Water | Product | Recovery |
|---|---|---|---|---|---|---|
| Exp. No. | Purity | Amt. | Amount | Amount | Purity | Rate |
| A | 13.9% | 3 g | 60 ml | 120 ml | 53.0% | 93.8% |
| B | 13.9% | 3 g | 60 ml | 135 ml | 49.1% | 95.9% |
| C | 13.9% | 3 g | 60 ml | 150 ml | 50.0% | 96.4% |

Optimizing the amount of aqueous solvent to use in the acetone/water precipitation step is important when preparing acetone mixtures that differ from the acetone mixture obtained from a silica column as described above, or when using an aqueous solvent containing less than 90% water. One of ordinary skill in the art can readily evaluate an optimal acetone-to-water ratio for a given acetone mixture by mixing the acetone mixture with various amounts of aqueous solvent, recovering a precipitate and testing for recovery, purity and composition by a standard procedure such as HPLC or TLC. It is anticipated that an optimal acetone to water ratio may differ according to a number of variables including, but not limited to, the source of the paclitaxel-containing material, solvent systems used in preparation of intermediate extracts, prior purification steps used in preparing the acetone mixture and the constituent composition of solids present in the acetone mixture. To illustrate, acetone mixtures prepared by extracting paclitaxel-containing material in the presence of a solvent, such as 70% ethanol as described in U.S. Pat. Nos. 5,279,949 and 5,478,736 to Nair are expected to have more water soluble components than an extract previously treated by precipitation in the presence of toluene or ether as described by Zamir in PCT No. WO 98/07712. Similarly, extracts prepared by multiple alcohol/water precipitations as described in PCT. Publication No. WO 96/34973 by Hong are likely to contain less water soluble material than the acetone mixture prepared from the silica column eluate described in the present invention.

Another important variable to optimize in the acetone/water precipitation step is the amount of acetone used to dissolve the 10% extract so as to obtain a concentration that ensures good recovery and enriched product in the precipitation step. Table 2 illustrates that in using the same acetone/water ratio (1:2), when the amount of acetone used produced a solids concentration of 1 g/5 mL, paclitaxel failed to precipitate, while a slightly lower solids concentration of 1 g/10 mL results in a high recovery but relatively low purity product (42.5%). Further, a solids concentration of at least 1 g/20 mL provides a recovery rate of about 97% and purity of 51.1%, while a still lower solids concentration of 1 g/25 mL results in a lower recovery of about 90%. Therefore, in a typical embodiment of the acetone/water precipitation step, the solids are dissolved in an amount of acetone to yield a solids concentration of about 1 g/20 mL (50 g/L).

TABLE 2

| Exp. No. | Starting Material | | Acetone | Water | Product Purity | Recovery Rate |
| --- | --- | --- | --- | --- | --- | --- |
| | Purity | Amt. | Amount | Amount | | |
| D | 12.8% | 1 g | 5 ml | 10 ml | — | — |
| E | 12.8% | 1 g | 10 ml | 20 ml | 42.5% | 100.1% |
| F | 12.8% | 1 g | 15 ml | 30 ml | 46.0% | 91.4% |
| G | 12.8% | 1 g | 20 ml | 40 ml | 51.1% | 97.1% |
| H | 12.8% | 1 g | 25 ml | 50 ml | 53.0% | 89.7% |

Another observation of the present invention is that the recovery rate and the purity of the product from the acetone/water precipitation step are dependent on the purity of paclitaxel in the acetone mixture. Table 3 illustrates that the acetone mixture purity ranging from 11–16% results in the recovery rate of 91–96% and purity of 46– 56%, while the acetone mixture purity below 10% provides the recovery rate of below 93% and purity of below 43%. Thus, various embodiments of this invention include an acetone/water purification step wherein the recovery of paclitaxel in the precipitates is at least 90% or more preferably, at least 95%.

TABLE 3

| Exp. No. | Starting Material Purity | Crystallized Product Purity | Yield |
| --- | --- | --- | --- |
| I | 16.1% | 55.2% | 94.2% |
| J | 15.7% | 53.0% | 93.1% |
| K | 14.6% | 49.6% | 94.1% |
| L | 13.9% | 48.9% | 93.7% |
| M | 13.8% | 51.7% | 95.2% |
| N | 12.9% | 47.1% | 94.7% |
| O | 12.2% | 45.9% | 93.3% |
| P | 11.0% | 46.3% | 91.6% |
| Q | 9.7% | 42.9% | 89.8% |
| R | 8.7% | 39.1% | 90.6% |
| S | 8.5% | 37.3% | 92.3% |
| T | 7.6% | 32.9% | 87.9% |
| U | 4.6% | 27.2% | 90.6% |

Prior methods using acetone in a binary solvent precipitation step have proven to be unsatisfactory. This may be because these procedures have used acetone/hexane to precipitate impurities rather than to precipitate paclitaxel, or have been used in conjunction with extracts containing less than 5% paclitaxel or have used acetone with other solvents such as pentane that do not yield effective purification. For example experiments with crude extracts containing 13.8% paclitaxel failed to precipitate with an acetone/pentane solvent system. When the paclitaxel content is increased to 29.3% or 50%, a pentane precipitate having a reasonable purity of 45% or 50% was obtained, but the recovery yield of 50% or 77% was poor, which makes the process impractical for commercial production. Similarly, attempts to use hexane and acetone to precipitate unwanted impurities from a crude extract were found to be inefficient. Although this step consistently removed certain undesirable compounds such as waxes, lipids, pigments, and sterols from a crude extract, the amount of impurities removed was minimal, hence making this step impractical for manufacturing. Other results demonstrated that acetone/hexane treatment did not provide a significant purity improvement, typically, the purity increase was only approximately 10%, from 1.65% to 1.8%. Hence, the acetone/water precipitation method provided herein has substantial advantages over prior acetone based precipitation methods.

The acetone/water precipitation step provided herein can be embodied in several paclitaxel isolation procedures. In one embodiment, acetone/water precipitation is used after at least one chromatography step. In another embodiment, the acetone/water precipitation step is used midway in a paclitaxel isolation procedure, for example, between a first silica chromatography step and a second chromatography step. In other embodiments, the acetone/water precipitation step may be incorporated into any procedure that produces an extract comprising at least 5% paclitaxel. When used midway through an isolation procedure, the step produces high yield and high purification at an early phase of paclitaxel isolation which facilitates subsequent purification steps. The acetone/water precipitation makes large scale production of paclitaxel technically and economically practical because of its simplicity, low cost, and high efficiency.

6) Second Silica Chromatography and First Crystallization

In a further embodiment of this invention, the material obtained from the acetone/water precipitation comprising at least 40% paclitaxel is further purified by conventional silica chromatography using a methylene chloride/ethylacetate elution solvent system similar to a system described in U.S. Pat. Nos. 5,618,538 and 5,480,639 to ElSohly et al. The distinctive features of the second silica chromatography step of the present invention pertain to the feed material and to the scale of operation. The feed material for the second silica chromatography column of the present invention is a large scale preparation comprising at least 40% paclitaxel obtained from the acetone/water precipitation step and typically containing 1.5–2.0 kg of solids. This material is dissolved in 5–7 L of methylene chloride and applied to a 12-in×10-ft silica gel column packed in a stainless steel pipe. Preferably a layer of Celite is added to the top of the column to prefilter the feed material. The column is eluted with a mobile phase comprising a gradient of methylene chloride to 50% methylene chloride/ethyl acetate, and fractions are collected. Fractions are pooled to obtain a heart cut with at least 65% paclitaxel and less than 1% cephalomannine with typical yields of 92%–95% of the paclitaxel present in the feed material.

The second silica column eluate is then concentrated by evaporation, lyophilized, redissolved in acetone then diluted with two volumes of pentane with stirring at 4° C. to give a first crystalline solid. The first crystalline solid is collected by filtration and dried. The first crystalline solid typically yields 90–95% of the paclitaxel present in the second silica column eluate and contains 85–96% paclitaxel and less than 1% cephalomannine.

7) Third Silica Chromatography and Second Crystallization

The first crystalline solid obtained from the second silica chromatography step contains at least 85% paclitaxel and this is further purified by a third silica chromatography step using a methylene chloride/ethyl acetate elution solvent. The third silica chromatography column of the present invention is designed for large scale separation of a sample typically containing 600–900 g of solids. In one embodiment, this material is dissolved in 2–4 L of methylene chloride and applied to a 12-in×10-ft silica gel column packed in a stainless steel pipe. The column is eluted with a gradient from 100% methylene chloride to 50% methylene chloride/ethyl acetate or with an isocratic mixture of methylene chloride and ethyl acetate. Fractions are collected and heart cut fractions containing more than 90% paclitaxel are pooled to obtain a third silica column eluate. The third silica column eluate typically yields 92–95% of the feed paclitaxel and contains 90–98% paclitaxel and less than 0.1% cephalomannine.

The third silica column eluate is then concentrated by evaporation, lyophilized, redissolved in acetone then diluted with two volumes of pentane with stirring at 4° C. to give a second crystalline solid. The second crystalline solid is collected by filtration and dried. The second crystalline solid typically recovers 90–95% of the paclitaxel present in the third silica column eluate and is comprised of greater than 98.5% paclitaxel with no individual taxane impurity greater than 0.2%.

8) A Representative Overall Method

As mentioned above, certain methods of the present invention, such as those related to the first silica chromatography step to obtain an acetone mixture containing 10% paclitaxel, and the use of acetone/water precipitation to obtain an extract containing of at least 40% paclitaxel, may be incorporated into other paclitaxel isolation procedures and therefore stand as separate embodiments of this invention. In another embodiment, the methods provided herein are combined to provide an overall procedure for the isolation of pharmaceutical grade paclitaxel from paclitaxel-containing material.

In this regard, one embodiment of this invention provides a paclitaxel isolation method that includes the steps of:

a) extracting the paclitaxel-containing material with methanol to obtain a methanol extract;

b) partitioning the methanol extract by liquid-liquid extraction of the methanol extract with methylene chloride and water to form a two phase system having a methanolic phase comprised of methanol/water and a methylene chloride phase comprised of methylene chloride and paclitaxel;

c) removing methanol and water from the methylene chloride phase to obtain a concentrated extract comprised of at least 1% paclitaxel, not more than about 5% (v/v) methanol, and not more than about 1% (v/v) water;

d) contacting the concentrated extract with a first silica matrix and eluting the first silica matrix to obtain a first eluate containing at least 10% paclitaxel;

e) adding acetone to the first eluate to obtain an acetone mixture;

f) contacting the acetone mixture with an aqueous solvent to form a precipitate containing at least 40% paclitaxel;

g) purifying paclitaxel from the precipitate by chromatography on a second silica column and eluting paclitaxel from the second silica column to form a second eluate containing at least 65% paclitaxel;

h) crystallizing the paclitaxel from the second eluate by mixing the second eluate with pentane to form a first crystalline solid containing at least 85% paclitaxel;

i) purifying paclitaxel from the first crystalline solid by chromatography on a third silica column and eluting paclitaxel from the third silica column to obtain a third eluate containing at least 90% paclitaxel; and j) crystallizing paclitaxel from the third eluate by mixing the second eluate with pentane to form a second crystalline solid containing at least 98.5% paclitaxel.

The advantages of high yield and high purity using conventional techniques make this overall procedure suitable for industrial scale production. An example of representative ranges of yield and purification obtainable by employing this procedure is shown in Table 4.

TABLE 4

|  | Paclitaxel Yield % | Paclitaxel Purity % (w/w) |
|---|---|---|
| Starting Paclitaxel-containing material (e.g., bark) | 100 | 0.02 |
| Methanol extract | 93–98 | 0.2 |
| Liquid-Liquid extraction | 95–97 | 1–4 |
| First Silica Column | 90–96 | 10–16 |
| Acetone/Water Precipitation | 90–98 | 45–55 |
| Second Silica Column | 92–95 | 65–75 |
| First Crystallization | 90–95 | 85–96 |
| Third Silica Column | 92–95 | 90–98 |
| Second Crystallization | 90–95 | 98.5–99.9 |
| Overall | 49–73 | 98.5–99.9 |

An additional advantage of this invention is that it provides for reproducible preparation of a bulk paclitaxel composition of exceptional and unique purity. To this end, the paclitaxel composition of the present invention comprises a novel ratio of paclitaxel in relation to other taxane impurities, and these ratios are not obtained by other known methods of paclitaxel preparation. In particular, the paclitaxel composition provided herein is distinct from, and superior to, other paclitaxel compositions presently available as drug products prepared by other large scale isolation methods, or prepared by semi-synthetic procedures. To illustrate this difference, Table 5 presents the analysis of a paclitaxel composition of the present invention compared with paclitaxel compositions of drug products available from other sources (i.e., as prepared by Bristol-Myers Squibb ("BMS"), Princeton, N.J.) In the following Table 5, the designation "IDP" refers to a drug product isolated by a method employed by BMS, while the designation "SDP" refers to a BMS drug product that is believed to be prepared by a semi-synthetic method which combines natural product isolation with at least one synthetic step. The designation "BDS" refers to a bulk drug substance isolated by the method of the present invention.

TABLE 5

| Sample | Type | Paclitaxel | 10-DAT | Cephalo-mannine | 7-epi-10 DAT | Taxol-C | 7-epi-Paclitaxel | Total Taxane Impurities* |
|---|---|---|---|---|---|---|---|---|
| BSF08A | IDP | >98.5 | 0.00 | 0.07 | 0.03 | 0.00 | 0.05 | 0.18 |
| D5F11A | IDP | >98.5 | 0.02 | 0.07 | 0.04 | 0.00 | 0.06 | 0.23 |
| M4F16A | IDP | >98.5 | 0.00 | 0.06 | 0.02 | 0.00 | 0.04 | 0.15 |
| A5F28A | IDP | >98.5 | 0.02 | 0.06 | 0.04 | 0.00 | 0.15 | 0.32 |
| C5F20E | IDP | >98.5 | 0.03 | 0.12 | 0.01 | 0.00 | 0.08 | 0.27 |
| KF506C | SDP | >98.5 | 0.29 | 0.20 | <0.01 | 0.00 | 0.08 | 0.59 |
| L5F28D | SDP | >98.5 | 0.12 | 0.16 | <0.01 | 0.00 | 0.05 | 0.34 |

TABLE 5-continued

| Sample | Type | Paclitaxel | 10-DAT | Cephalo-mannine | 7-epi-10 DAT | Taxol-C | 7-epi-Paclitaxel | Total Taxane Impurities* |
|---|---|---|---|---|---|---|---|---|
| A6F07A | SDP | >98.5 | 0.15 | 0.16 | 0.02 | 0.00 | 0.04 | 0.38 |
| L5F28A | SDP | >98.5 | 0.14 | 0.15 | 0.01 | 0.00 | 0.04 | 0.36 |
| L6F2SA | SDP | >98.5 | 0.29 | 0.11 | 0.00 | 0.00 | 0.01 | 0.42 |
| F8F38A | SDP | >98.5 | 0.18 | 0.15 | 0.00 | 0.00 | 0.03 | 0.39 |
| J0120 | BDS | >99.5 | 0.00 | 0.02 | 0.00 | 0.00 | 0.03 | 0.08 |
| K0149 | BDS | >99.5 | 0.00 | 0.02 | 0.00 | 0.00 | 0.03 | 0.07 |
| M0167 | BDS | >99.5 | 0.00 | 0.01 | 0.00 | 0.07 | 0.00 | 0.09 |
| E0084 | BDS | >99.5 | 0.00 | 0.03 | 0.00 | 0.00 | 0.00 | 0.07 |
| F0100 | BDS | >99.5 | 0.00 | 0.03 | 0.00 | 0.00 | 0.00 | 0.07 |
| F0103 | BDS | >99.5 | 0.00 | 0.03 | 0.00 | 0.00 | 0.00 | 0.06 |

*Total Taxane Impurities include baccatin-III and other non-identified taxane peaks which are not specifically listed in this table.

The data of Table 5 demonstrate that, in addition to providing a paclitaxel isolation method that enables routine isolation of paclitaxel of greater than 99.5% purity, the present invention also provides a unique paclitaxel composition. In one aspect, the paclitaxel composition of this invention comprises at least 99.5% paclitaxel with total taxane impurities of less than 0.14% and, more specifically, with total taxane impurities from about 0.05% to 0.14%. More typically, the total taxane impurities are from 0.06% to 0.09%. In certain embodiments, the paclitaxel composition contains at least 99.5% paclitaxel with from 0.01% to 0.05% cephalomannine, and more typically from 0.01% to 0.03% cephalomannine. In related aspects, the paclitaxel composition contains the aforementioned concentrations of paclitaxel and cephalomannine, and further contains no detectable levels of 10-DAT, 7-epi-10 DAT, and Taxol C. Such compositions may be prepared according to the overall method provided by this invention. These compositions may further be formulated with a pharmaceutically acceptable carrier or diluent in order to provide a pharmaceutical composition suitable for therapeutic delivery.

The compositions of this invention are not encountered in typical laboratory-scale purification which seek to produce paclitaxel at 100% purity. This is accomplished in the laboratory by a step which removes cephalomannine to a level of less than 0.01% and/or total taxane impurities to a level of less than 0.05%. Further, the paclitaxel-containing material used as the "feed" for such laboratory-scale purification do not contain total taxane impurities in the range from 0.05% to 0.14% and/or cephalomannine at a level from 0.01% to 0.05%, but rather contain much higher amounts of both total taxane impurities and/or cephalomannine. In addition, as previously discussed, such laboratory scale procedures are not economical for large scale production methods.

Similarly, the compositions of this invention are not encountered in ordinary large-scale production procedures because, as illustrated in Table 5, while such procedures can produce compositions containing paclitaxel at levels of greater than 98.5%, they contain a distinctly different (and less desirable) constituency of taxane impurities than provided by the compositions of the present invention.

9) Large Scale Chromatography

A related aspect of this invention is the use of large dimension columns suitable for industrial scale high performance chromatography at medium pressures. As used herein, large dimension columns have an interior diameter of at least 1 inch. The columns used in one embodiment of this invention have a diameter of 1.25–1.35 inches. In a larger scale embodiment, the columns have a diameter of 6 to 18 inches. The column length can be 1–20 feet. The preferred length for large scale is about 10 feet. Large dimension columns have previously been impractical for industrial scale procedures for a variety of reasons including expense of fabrication, difficulty in establishing reproducible packing procedures, difficulty in reproducible medium and high pressure operation, and safety in solvent removal. These impracticalities are seldom encountered in laboratory scale techniques, because the scale allows for greater flexibility in the design and has less stringent economic requirements.

The present invention provides a design that uses materials which are readily obtained from commercial sources or easily fabricated therefrom so as to make large dimension high performance columns economically practical. The design further includes features that accommodate safety needs, and packing methods to provide durable large scale columns that give reproducible performance and which can be economically maintained.

To provide for reproducible packing of large bed volumes, the columns are fitted with one or more vibrators to enable an even and reproducible packing of the column matrix material. Reproducible packing is critical for high performance chromatography, especially when using large scales columns. In a preferred practice, these columns are packed with fresh silica before each use.

Fast and efficient removal of the column matrix requires a thorough and dependable drying of the column matrix. This is especially important when an organic solvent has passed through the matrix. The columns of the present invention are equipped with a self regulating heat trace cable to provide heat to the columns, thus providing for controlled and safe evaporation of organic solvent. The heat trace cable will heat the column, thus accelerating the evaporation of the solvent in the matrix. A gas, preferably nitrogen, is passed through the column to remove the evaporated solvent to achieve a dry matrix. Optionally, the drying process may include passing heated air or nitrogen through the column matrix from one of the two inlets/outlets, or applying vacuum to the column. Once dried, the column matrix is efficiently removed by detaching the one of the flanges and applying an even pressure to the opposite end. Alternatively, the column matrix may be removed by suction.

As is apparent from the foregoing description, practice of the present invention may be embodied in a variety of compositions and methods related to the isolation of paclitaxel from paclitaxel-containing material. The following Examples are offered by way of illustration and not by way of limitation.

EXAMPLES

Example 1

Large Scale Methanol Extraction of Yew Bark

Extraction of paclitaxel from Yew bark was carried out in a temperature controlled custom built 22,000 L jacketed extraction tank with a fiber filter system designed for percolating process. This system has the capability to be utilized as a reactor to quantitatively extract paclitaxel by solvent extraction with large volume of flammable solvent in a safe manner. The vessel has a port whereby the bark is transported from the biomass storage container directly to the extraction tank preventing fine particles from escaping into the plant. A coarse filter was installed at the bottom of the tank to retain the spent bark but allowing methanol to circulate. A stainless steel frame is made to hold a filter.

A pneumatic transportation system acts to transport fresh bark as well as in the removal of spent Yew bark. Another port is designed for the introduction of inert nitrogen gas which act as a blanket above the methanol for safety purposes. The extraction tanks were charged with bark using a screw conveyor system which deposits dry bark into the tanks through a 6 inch diameter hole centered in the upper head of the tanks. Methanol is transferred into the tank before bark is added.

A static bark distributor was mounted permanently inside the upper head of the extraction tanks, just below the bark inlet chute. The distributor was installed to permit the distribution of bark uniformly in the extraction vessels as designed and is maintenance free. Effective extraction was achieved by percolating bark with 12,000 liters of methanol for 3 days at 40° C. 2,000 lbs. of processed bark produced 10,000 liters of methanolic bark extract. This large volume was further reduced in volume by evaporation using a wiped film evaporator.

Example 2

Large Scale Liquid-liquid Extraction

A concentrated methanol extract containing about 0.2% paclitaxel was extracted with methylene chloride in a 6,000 liter partition vessel with an impeller to separate the preferentially water/methanol soluble compounds from the preferentially methylene chloride soluble compounds contained in the concentrated methanol extract.

The solvents were mixed in the following ratio: 924 L of concentrated methanol extract: 1103 L of methylene chloride: 450 L of tap water. After allowing for the solvent to partition, 946 L of methylene chloride layer containing paclitaxel was separated into a two phase solution. The bottom methylene chloride phase having a clear dark ruby color was retained while the upper layer having an olive green color was discarded. This methylene chloride extract was then concentrated by evaporation. Analyses of the methylene chloride concentrate demonstrated a paclitaxel content of 2–3% with a yield of more than 90%.

Example 3

First Silica Column Chromatography Step to Produce an Extract Comprised of 10% Paclitaxel Experiments were conducted to evaluate certain critical parameters impacting chromatographic performance including, the number and composition of mobile phase gradient steps, the purity of paclitaxel-containing feed material, and the mobile phase flow rate. These parameters were investigated to find the simplest and least expensive process for producing an extract of acceptable purity. Initial experiments were conducted in glass gravity columns and then as parametric ranges were narrowed, experiments moved to stainless steel columns.

Table 6 summarizes the results of one set of experiments to determine the optimum solvent composition for the chromatographic process. These experiments indicated that use of an isocratic solvent system comprising hexane:acetone mixtures of to 70:30 to 75:25 gives an efficient separation.

TABLE 6

| Exp. No. | Paclitaxel Feed Purity (%) | Solvents Hexane/ Acetone | Column Dimension | Heart Cut Purity w/w % | Recovery Rate |
|---|---|---|---|---|---|
| W | 2.6% | 70:30 | 1.6 × 10.7 cm | 13.2% | 99% |
| Y | 1.64% | 72.5:27.5 | 1.6 × 10.7 cm | 10.8% | 97% |
| Z | 1.77% | 75:25 | 3.5 × 300 cm | 12.8% | 96% |
| AA | 1.77% | 75:25 | 3.5 × 30 cm | 15.1% | 99% |
| AB | 1.77% | 75:25 | 3.5 × 300 cm | 13.5% | 86% |
| AC | 1.64% | 75:25 | 0.8 × 50 cm | 15.0% | 101% |
| AD | 1.38% | 74:26 | 0.8 × 50 cm | 10.6% | 96% |
| AE | 1.38% | 74:26 | 3.5 × 300 cm | 11.2% | 98% |
| AF | 2.72% | 74:26 | 0.8 × 50 cm | 18.8% | 98% |
| AG | 2.33% | 74:26 | 0.8 × 50 cm | 19.0% | 97% |

The following laboratory scale experiment was carried out to study the effects of methanol and water on column performance. Feeds with varying methanol concentrations of 2.3%, 5.0% and 9.9% were chromatographed on a pilot column. Results of the heart cut fraction, purification and the recovery yield of each experiment were recorded (Table 7). It was determined that feeds with high methanol content affect the chromatographic separation adversely and the best separation was obtained with feeds containing less than 5% methanol. The combination of methanol and water was also studied, and combinations in the ranges of 0–5% for methanol and 0–2% for water worked particularly well. A typical satisfactory feed combination comprises 310 gm/L of solids, 4% methanol and 0.5% water.

TABLE 7

| | Experiments on Feed Material Optimization | | | | |
|---|---|---|---|---|---|
| Exp. No. | MeOH Concentration | Water Concentration | Heart-cut Fractions | HC Purity w/w % | Recovery Rate |
| AH | 9.9% | 2.0% | F21–69 | 10.9% | 89% |
| AI | 0% | 0.1% | F37–74+ | 15.7% | 94% |
| AJ | 5.0% | 1.0% | F29–69 | 14.7% | 98% |
| AK | 5.0% | 1.0% | F33–69 | 15.8% | 97% |
| AL | 5.0% | 1.0% | F31–69 | 13.6% | 93% |
| AM | 2.5% | 1.0% | F35–80+ | 14.8% | 99% |
| AN | 5.0% | 0.5% | F27–64 | 14.0% | 97% |
| AO | 5.0% | 0.5% | F34–68+ | 15.9% | 97% |
| AP | 4.0% | 0.5% | F27–65 | 16.8% | 99% |
| AQ | 4.0% | 0.1% | F23–57 | 13.5% | 99% |

Example 4

Scale-up Experiments

Scaling-up experiments were conducted on a full length column (1.35 inch×10 ft.) using:

1) Isocratic Solvent System: Hexane:Acetone 74:26
2) Feed Material containing about 2% paclitaxel 3) Total Solids in the Feed: 252 g
4) Solids Content of the Feed: 310 g/L
5) MeOH Concentration in the Feed: 4.0% v/v
6) Water Concentration in the Feed: 0.5% v/v
7) Packing the column with silica and a layer of Celite on the top.
8) Heart-cut Fractions Specification: 2.0% w/w paclitaxel for the inclusive fractions The results of these experiments are summarized in Table 8:

TABLE 8

Results from Scale-up Development Runs

| Exp. No. | HC Fractions | HC Purity | Purification Factor | Recovery Rate | Loading Time |
|---|---|---|---|---|---|
| AP | F25–62 | 12.2% | 5.5 | 96% | 1h 40 min w/o Celite |
| AQ | F24–71+ | 11.5% | 5.2 | ~100% | 52 min w/Celite |
| AR | F27–66 | 13.8% | 6.2 | ~100% | 58 min w/Celite |
| AS | F25–65 | 13.4% | 5.8 | ~100% | 50 min w/Celite |

Loading difficulties were encountered during the scale-up runs based on a 1.35 inch×10 feet stainless steel column. Several attempts were made to improve the loading of 2% crude paclitaxel extract including the addition of a pre-filtration step, equilibrating the column with DCM, and filtration through Celite. The most successful results were obtained by adding a Celite layer on the top of the column above the silica bed.

Results from Table 8 indicated that all four runs produced heart-cut fractions having a purity ranging from 11.5% to 13.8% and a recovery rate of greater than 95%.

Example 5

Acetone/Water Precipitation to Produce 50% Paclitaxel From a 10% Extract 715 g of 15.7% w/w paclitaxel extract was dissolved in 14.3 L of acetone. A precipitate was generated by mixing the paclitaxel solution with 35.75 L of water, and stirring over night. The precipitate was collected by filtration and rinsed on the filter with 2 l of water. The dried precipitate weighed 197 g and contained 55.85% w/w of paclitaxel.

What is claimed is:

1. A method of isolating paclitaxel from a paclitaxel extract comprising the steps of:
   adding acetone to the paclitaxel extract to form an acetone mixture;
   contacting the acetone mixture with an aqueous solvent to form a precipitate, wherein the precipitate has a paclitaxel purity that is at least 3 times higher than the paclitaxel purity in the paclitaxel extract; and
   recovering the precipitate.

2. The method in claim 1 wherein the paclitaxel extract contains at least 5% (w/w) of paclitaxel and the precipitate comprises at least 20% (w/w) of paclitaxel.

3. The method in claim 1 wherein the paclitaxel extract contains at least 10% (w/w) of paclitaxel and the precipitate comprises at least 40% (w/w) of paclitaxel.

4. The method of claim 1 wherein the precipitate has a paclitaxel purity that is at least 4 times higher than the paclitaxel purity in the paclitaxel extract.

5. The method of claim 1 wherein the paclitaxel extract is obtained from a paclitaxel-containing material.

6. The method of claim 5 wherein the paclitaxel-containing material comprises tissue from a species of a Taxus genus.

7. The method of claim 5 wherein the paclitaxel-containing material is obtained from a cell culture containing tissue cultured from a species of the genus Taxus.

8. The method of claim 7 wherein the paclitaxel-containing material comprises a root culture.

9. The method of claim 7 wherein the paclitaxel-containing material is the tissue of the cell culture.

10. The method of claim 7 wherein the paclitaxel-containing material is a media in which the cell culture is grown.

11. The method of claim 6 wherein the paclitaxel-containing material comprises tissue from the species $T.$ brevifolia, $T.$ yunnanensis, $T.$ x media dark green spreader, $T.$ x media Hill, $T.$ x media Hicksii, $T.$ cuspidata $T.$ chinensis, $T.$ wallichiana, $T.$ canadensis, $T.$ globosa and $T.$ sumatrana or mixtures thereof.

12. The method of claim 11 wherein the tissue comprises bark and the species is $T.$ brevifolia, or $T.$ yunnanensis.

13. The method of claim 11 wherein the tissue comprises roots and the species is $T.$ x media dark green spreader, $T.$ x media Hill, $T.$ x media Hicksii or $T.$ cuspidata.

14. The method of claim 11 wherein the tissue comprises needles and the species is $T.$ x media dark green spreader, $T.$ x media Hill, $T.$ x media Hicksii, $T.$ cuspidata, or $T.$ canadensis.

15. The method of claim 5 wherein the paclitaxel-containing material is a microorganism that produces paclitaxel.

16. The method of claim 15 wherein the microorganism is a species of *Erwinia taxi* or *Taxomyces andreanae*.

17. The method of claim 1 wherein the paclitaxel extract is obtained by eluting paclitaxel from at least one chromatography matrix.

18. The method of claim 17 wherein the chromatography matrix is a silica matrix.

19. The method of claim 1 wherein the paclitaxel extract is obtained by performing at least two precipitations of paclitaxel from a mixture containing an organic solvent.

20. The method of claim 1 wherein the paclitaxel extract is obtained by eluting paclitaxel from at least one chromatography matrix and performing at least one precipitation of paclitaxel from a mixture containing an organic solvent.

21. The method of any one of claims 17–20 wherein obtaining the paclitaxel extract further includes performing at least one liquid-liquid extraction with an organic solvent to form a two phase solution wherein one phase is enriched with paclitaxel.

22. The method of claim 1 wherein the aqueous solvent is at least 50% (v/v) water.

23. The method of claim 1 wherein the aqueous solvent is at least 70% (v/v) water.

24. The method of claim 1 wherein the aqueous solvent is at least 90% (v/v) water.

25. The method of claim 1 wherein the aqueous solvent consists essentially of water.

26. The method of any one of the claims 22–25, wherein the aqueous solvent is buffered.

27. The method of claim 1 wherein 1 to 5 volumes of aqueous solvent is mixed with 1 volume of the acetone mixture.

28. The method of claim 1 wherein 2 to 3 volumes of aqueous solvent is mixed with 1 volume of the acetone mixture.

29. The method of claim 1 wherein about 2.5 volumes of aqueous solvent is mixed with 1 volume of the acetone mixture.

30. The method of claim 1 wherein the precipitate contains an amount of impurities less than an amount of impurities contained in the acetone mixture.

31. The method of claim 30 wherein the amount of impurities contained in the precipitate is at least 50% less than the amount of impurities contained in the acetone mixture.

32. The method of claim 30 wherein the amount of impurities contained in the precipitate is at least 75% less than the amount of impurities contained in the acetone mixture.

33. The method of claim 1 wherein the precipitate contains at least 90% of the paclitaxel present in the acetone mixture.

34. The method of claim 1 wherein the precipitate contains at least 95% of the paclitaxel present in the acetone mixture.

35. A method of making an acetone mixture containing at least 5% (w/w) paclitaxel comprising the steps of:
 a) extracting paclitaxel-containing material containing at least 0.005% paclitaxel with methanol to obtain a methanol extract;
 b) performing liquid-liquid extraction of the methanol extract by mixing the methanol extract with methylene chloride and water to form a two phase system having a methanolic phase comprised of methanol/water and a methylene chloride phase comprised of methylene chloride and paclitaxel;
 c) removing methanol and water from the methylene chloride phase to obtain a concentrated extract comprised of at least 1% paclitaxel, not more than about 5% (v/v) methanol, and not more than about 1% (v/v) water;
 d) contacting the concentrated extract with a silica matrix then eluting the silica matrix to obtain an eluate containing at least 5% (w/w) paclitaxel; and
 e) adding acetone to the eluate to obtain the acetone mixture.

36. The method of claim 35 wherein the paclitaxel-containing material comprises tissue selected from the species *T. brevifolia, T. yunnanensis, T. x. media* dark green spreader, *T. x media* Hill, *T. x media Hicksii. T. cuspidata, T. chinensis, T. wallichiana, T. canadensis, T. globosa* and *T. sumatrana* and paclitaxel expressing microorganisms and cell culture.

37. The method of claim 35 wherein the acetone mixture contains at least 10% (w/w) paclitaxel.

38. The method of claim 35 wherein the acetone mixture contains at least 12.5% (w/w) paclitaxel.

39. The method of claim 35 wherein the acetone mixture contains at least 90% of the paclitaxel present in the concentrated extract.

40. The method of claim 35 wherein the concentrated extract has a methanol content ranging from 2.5% to 5% (v/v) and a water content ranging from 0.1% to 1% (v/v).

41. The method of claim 35 wherein, after step d) and before step e), the eluate containing at least 5% (w/w) paclitaxel is dried to a residue, and wherein adding the acetone at step e) dissolves paclitaxel contained in the residue.

42. A method for isolating paclitaxel from paclitaxel-containing material comprising the steps of:
 a) extracting the paclitaxel-containing material with methanol to obtain a methanol extract;
 b) partitioning the methanol extract by liquid-liquid extraction of the methanol extract with methylene chloride and water to form a two phase system having a methanolic phase comprised of methanol/water and a methylene chloride phase comprised of methylene chloride and paclitaxel;
 c) removing methanol and water from the methylene chloride phase to obtain a concentrated extract comprised of at least 1% paclitaxel, not more than about 5% (v/v) methanol, and not more than about 1% (v/v) water;
 d) contacting the concentrated extract with a first silica matrix and eluting the first silica matrix to obtain a first eluate containing at least 10% paclitaxel;
 e) adding acetone to the first eluate to obtain an acetone mixture;
 f) contacting the acetone mixture with an aqueous solvent to form a precipitate containing at least 40% paclitaxel;
 g) purifying paclitaxel from the precipitate by chromatography on a second silica column and eluting paclitaxel from the second silica column to form a second eluate containing at least 65% paclitaxel;
 h) crystallizing the paclitaxel from the second eluate by mixing the second eluate with pentane to form a first crystalline solid containing at least 85% paclitaxel;
 i) purifying paclitaxel from the first crystalline solid by chromatography on a third silica column and eluting paclitaxel from the third silica column to obtain a third eluate containing at least 90% paclitaxel; and
 j) crystallizing paclitaxel from the third eluate by mixing the second eluate with pentane to form a second crystalline solid containing at least 98.5% paclitaxel.

43. The method of claim 42 wherein the paclitaxel-containing material contains at least 0.005% (w/w) paclitaxel.

44. The method of claim 42 wherein the paclitaxel-containing material contains at least 0.02% (w/w) paclitaxel.

45. The method of claim 42 wherein acetone is added to a concentrated residue of the first eluate.

46. The method of claim 42 wherein at least one of the first eluate, the second eluate and the third eluate is concentrated to a residue.

47. The method of claim 46 wherein at least one residue is dissolved in an organic solvent.

48. The method of claim 42 wherein the second crystalline solid contains at least 99.0% (w/w) paclitaxel.

49. The method of claim 42 wherein the second crystalline solid contains at least 99.5% (w/w) paclitaxel.

50. The method of claim 42 wherein the second crystalline solid contains at least 40% of the paclitaxel present in the starting paclitaxel-containing material.

51. The method of claim 42 wherein the second crystalline solid contains at least 60% of the paclitaxel present in the starting paclitaxel-containing material.

52. The method of any one of claims 42–51 wherein the second crystalline solid contains less than 0.2% (w/w) of any individual taxane impurity.

53. The method of claim 52 wherein the second crystalline solid contains less than 0.1% (w/w) of any individual taxane impurity.

54. The method of claim 52 wherein the second crystalline solid contains less than 0.05% (w/w) of any individual taxane impurity.

55. The method of claim 42 wherein an amount of paclitaxel is recovered in each of steps b–j that is at least 90% of an amount of paclitaxel present in an immediately preceding step.

56. A paclitaxel composition comprising at least 99.5% paclitaxel and having total taxane impurities ranging from 0.05% to 0.14%.

57. The paclitaxel composition of claim 56 having total taxane impurities ranging from 0.06% to 0.09%.

58. The paclitaxel composition of claim 56 comprising 0.01% to 0.05% cephalomannine as a taxane impurity.

59. The paclitaxel composition of claim 58 comprising 0.01% to 0.03% cephalomannine as a taxane impurity.

60. The paclitaxel composition of claim 56 comprising less than 0.01% 10-DAT, 7-epi-10-DAT, and 7-epi-paclitaxel.

61. A pharmaceutical composition comprising the paclitaxel composition of claim 56 admixed with a pharmaceutically acceptable carrier or diluent.

* * * * *